United States Patent
Ledden

(10) Patent No.: US 10,371,661 B2
(45) Date of Patent: Aug. 6, 2019

(54) LUMINESCENT OXYGEN CHANNELING IMMUNOASSAYS UTILIZING ELECTROCHEMICAL DISCHARGE OF SINGLET OXYGEN AND METHODS OF PRODUCTION AND USE THEREOF

(71) Applicant: Siemens Healthcare Diagnostics Inc., Tarrytown, NY (US)

(72) Inventor: David J. Ledden, Medway, MA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 623 days.

(21) Appl. No.: 14/776,164

(22) PCT Filed: Mar. 14, 2014

(86) PCT No.: PCT/US2014/027025
§ 371 (c)(1),
(2) Date: Sep. 14, 2015

(87) PCT Pub. No.: WO2014/152165
PCT Pub. Date: Sep. 25, 2014

(65) Prior Publication Data
US 2016/0033443 A1 Feb. 4, 2016

Related U.S. Application Data

(60) Provisional application No. 61/788,692, filed on Mar. 15, 2013.

(51) Int. Cl.
*G01N 27/327* (2006.01)
*G01N 33/543* (2006.01)
*G01N 33/542* (2006.01)

(52) U.S. Cl.
CPC ....... *G01N 27/3275* (2013.01); *G01N 33/542* (2013.01); *G01N 33/5438* (2013.01)

(58) Field of Classification Search
CPC .......... G01N 27/3275; G01N 33/5306; G01N 33/582; G01N 33/5438; G01N 33/542; G01N 33/533; G01N 33/54386; G01N 33/585; G01N 21/76; B01L 3/5027; B01L 3/502761; B01L 3/502769
See application file for complete search history.

(56) References Cited

U.S. PATENT DOCUMENTS

| | | | |
|---|---|---|---|
| 4,277,437 A | 7/1981 | Maggio | |
| 5,340,716 A | 8/1994 | Ullman et al. | |
| 6,198,950 B1* | 3/2001 | Kraus | A61B 5/14532 128/903 |
| 2002/0197649 A1 | 12/2002 | Singh | |
| 2006/0118496 A1* | 6/2006 | Nuttall | C02F 1/70 210/748.09 |
| 2007/0020678 A1 | 1/2007 | Ault-Riche et al. | |
| 2008/0164154 A1 | 7/2008 | Purvis | |
| 2009/0068637 A1 | 3/2009 | Xia et al. | |
| 2009/0130771 A1* | 5/2009 | Davies | G01N 33/54326 436/149 |
| 2010/0140086 A1* | 6/2010 | Sigal | B82Y 30/00 204/400 |
| 2010/0267077 A1* | 10/2010 | Patrice | G01N 33/84 435/29 |
| 2011/0053289 A1 | 3/2011 | Lowe et al. | |
| 2013/0041236 A1 | 2/2013 | Pugia et al. | |
| 2014/0308690 A1 | 10/2014 | Samproni | |
| 2018/0059105 A1* | 3/2018 | Lowe | G01N 33/558 |

FOREIGN PATENT DOCUMENTS

| | | |
|---|---|---|
| WO | 03012422 A1 | 2/2003 |
| WO | 2009146166 A2 | 12/2009 |
| WO | 2011143606 A1 | 11/2011 |
| WO | 2014151450 A1 | 9/2014 |

OTHER PUBLICATIONS

European Search Report and Written Opinion of European Application No. 14768580.4 dated Sep. 16, 2016.
Duran et al.,"Singlet oxygen formation 1-15 during peroxidase catalyzed degradation of carcinogenic N-nitrosamine", Jul. 14, 1978, Biochemical and Biophysical Research Communications, vol. 83; No. 1; pp. 287-294.
J. M. Aubry, "Search for singlet oxygen in the decomposition of hydrogen peroxide by mineral compounds in aqueous solutions", J. Am. Chem. Soc., 1985, 107 (21), pp. 5844-5849.
J. M. Aubry et al.,"Chemical sources of singlet oxygen. 3. Peroxidation of water-soluble singlet oxygen carriers with the hydrogen peroxide-molybdate system", J. Org. Chem., 1989, 54 (3), pp. 726-728.
Boehme et al., "Generation of Singlet Oxygen from Hydrogen Peroxide Disproportionation Catalyzed by Molybdate Ions", 1992, Inorg. Chem., 31, pp. 3468-3471.
Niu et al., "Singlet molecular oxygen generation from the decomposition of sodium peroxotungstate and sodium peroxomolybdate", Inorg. Chem., 1992, 31 (16), pp. 3472-3476.
Nardello et al.,"95Mo NMR and kinetic studies of peroxomolybdic intermediates involved in the catalytic disproportionation of hydrogen peroxide by molybdate ions", Inorg. Chem., 1995, 34 (20), pp. 4950-4957.
Aubry et al.,"Preparative Oxidation of Organic Compounds in Microemulsions with Singlet Oxygen Generated Chemically by the Sodium Molybdate/Hydrogen Peroxide System", J. Am. Chem. Soc., 1997, 119 (23), pp. 5286-5294.
Almeida et al.,"Direct evidence of singlet molecular oxygen [O 2 ( 1 Δ g ) ] production in the reaction of acetonitrile with hydrogen peroxide in alkaline solutions", 2003, Analytica Chimica Acta, 482(1), pp. 99-104.

(Continued)

*Primary Examiner* — Gurpreet Kaur
(74) *Attorney, Agent, or Firm* — Kyle D. Petaja

(57) ABSTRACT

Chemiluminescent detection systems, kits, and microfluidics devices containing same, as well as methods of production and use thereof, are disclosed.

17 Claims, 2 Drawing Sheets

(56) References Cited

OTHER PUBLICATIONS

International Search Report and Written Opinion of International Application No. PCT/US2014/027025 dated Jul. 30, 2014.
European Office Action of European Patent Application N. 18182375.8 dated Sep. 19, 2018.

* cited by examiner

LUMINESCENT OXYGEN CHANNELING IMMUNOASSAYS UTILIZING ELECTROCHEMICAL DISCHARGE OF SINGLET OXYGEN AND METHODS OF PRODUCTION AND USE THEREOF

CROSS REFERENCE TO RELATED APPLICATIONS/INCORPORATION BY REFERENCE STATEMENT

This application is the US National Stage of International Application No. PCT/US2014/027025, filed Mar. 14, 2014 and claims the benefit thereof. The International Application claims the benefit of U.S. Provisional Application No. 61/788,692, filed Mar. 15, 2013. All of the applications are incorporated by reference herein in their entirety.

BACKGROUND

Immunoassay technologies are widely used in the field of medical diagnostics. One example of a commercially used immunoassay is the induced luminescence immunoassay (LOCI®) technology. The induced luminescence immunoassay is described in U.S. Pat. No. 5,340,716 (Ullman), the entire contents of which are expressly incorporated herein by reference. The currently available LOCI® technology involves a homogeneous assay (i.e., no wash steps involved) that has high sensitivity, and the assay uses several reagents and requires that two of these reagents (referred to as a "sensibead" and a "chemibead") held by other immunoassay reagents to be in close proximity to achieve a signal. Upon exposure to light at a certain wavelength, the sensibead releases singlet oxygen, and if the two beads are in close proximity, the singlet oxygen is transferred to the chemibead; this causes a chemical reaction that results in the chemibead giving off light that can be measured at a different wavelength.

However, there are obstacles that exist for this technology. There are multiple factors that can contribute to background signal, such as but not limited to, (1) the nonspecifically binding of two beads to one another, and (2) the presence of two unattached beads that are simply in close proximity to one another. For these reasons, the final reaction mixture is diluted prior to light exposure to dissociate nonspecifically bound beads and to increase the mean particle distance between unbound beads. In addition, as the assay is homogeneous, plasma separation is required, and thus whole blood cannot be directly used in this diagnostic platform.

The presently disclosed and claimed inventive concept(s) is directed to new and improved compositions, assays, and methods of use thereof; this technology provides a heterogeneous assay format in which background signal is reduced or eliminated and plasma separation is not required.

DETAILED DESCRIPTION

Figure 1:
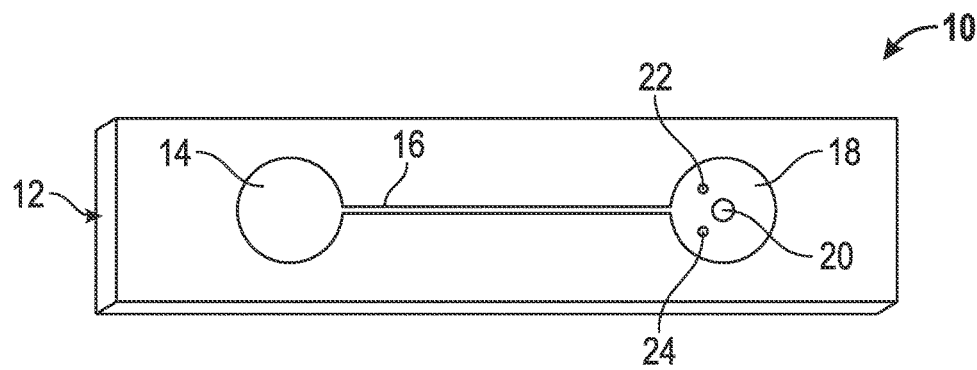
FIG. 1 illustrates one embodiment of a microfluidic device constructed in accordance with the presently disclosed and claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this presently disclosed and claimed inventive concept(s) have been described in terms of particular embodiments, it will be apparent to those of skill in the art that variations may be applied to the compositions and/or methods and in the steps or in the sequence of steps of the method described herein without departing from the concept, spirit, and scope of the presently disclosed and claimed inventive concept(s). All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, the phrase "associated with" includes covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

The term "purified" as used herein means at least one order of magnitude of purification is achieved compared to the starting material or of the natural material, for example but not by way of limitation, two, three, four or five orders of magnitude of purification of the starting material or of the natural material. Thus, the term "purified" as utilized herein does not necessarily mean that the material is 100% purified, and therefore such term does not exclude the presence of other material(s) present in the purified composition.

Throughout the specification and claims, unless the context requires otherwise, the terms "substantially" and "about" will be understood to not be limited to the specific terms qualified by these adjectives/adverbs, but allow for minor variations and/or deviations that do not result in a significant impact thereto. For example, in certain instances the term "about" is used to indicate that a value includes the inherent variation of error for the device, the method being employed to determine the value and/or the variation that exists among study subjects. Similarly, the term "substantially" may also relate to 80% or higher, such as 85% or higher, or 90% or higher, or 95% or higher, or 99% or higher, and the like.

The terms "analog" and "derivative" are used herein interchangeably and refer to a substance which comprises the same basic carbon skeleton and carbon functionality in its structure as a given compound, but can also contain one or more substitutions thereto. The term "substitution" as used herein will be understood to refer to the replacement of at least one substituent on a compound with a residue R. In certain non-limiting embodiments, R may include H, hydroxyl, thiol, a halogenid selected from fluoride, chloride, bromide or iodite, a C1-C4 compound selected one of the following: linear, branched or cyclic alkyl, optionally substituted, and linear branched or cyclic alkenyl, wherein the optional substitutents are selected from one or more alkenylalkyl, alkynylalkyl, cycloalkyl, cycloalkenylalkyl, arylalkyl, heteroarylalkyl, heterocyclealkyl, optionally substituted heterocycloalkenylalkyl, arylcycloalkyl, and arylheterocycloalkyl, each of which is optionally substituted wherein the optional substituents are selected from one or more of alkenylalkyl, alkynylalkyl, cycloalkyl, cyclalkenylalkyl, arylalkyl, alkylaryl, heteroarylalkyl, heterocyclealkyl, optionally substituted heterocycloakenylalkyl, arylcycloalkyl, and arylheterocyclalkyl, phenyl, cyano, hydroxyl, alkyl, aryl, cycloalkyl, cyano, alkoxy, alkylthio, amino, —NH (alkyl), —NH(cycloalkyl)2, carboxy and —C(O))-alkyl.

In particular embodiments, the term "analog" as used herein refers to a compound that binds to the same binding partner (i.e., antibody) as a target analyte but that is chemically different from the target analyte. For example but not by way of limitation, when the target analyte is a peptide, polypeptide, or protein, the target analyte may possess an epitope to which a binding partner binds (i.e., for indirect association of the singlet oxygen-activatable chemiluminescent composition and/or sensitizer with the target analyte). In this example, an analog of the target analyte possesses an epitope that is identical to the epitope of the target analyte that is recognized by the binding partner; therefore, the analog is capable of binding to the binding partner to which the target analyte binds, even through the analyte may have a different amino acid sequence than the target analyte and thus be less than 100% identical thereto.

The term "sample" as used herein will be understood to include any type of biological sample that may be utilized in accordance with the presently disclosed and claimed inventive concept(s). Examples of biological samples that may be utilized include, but are not limited to, whole blood or any portion thereof, plasma, serum, saliva, sputum, cerebrospinal fluid (CSF), skin, interstitial fluids, tears, mucus, urine, swabs, and the like.

The term "binding partner" as used herein will be understood to refer to any molecule capable of associating with another molecule. For example but not by way of limitation, the binding partner may be an antibody (including polyclonal or monoclonal antibodies), antibody fragments (such as but not limited to, Fab, Fab', F(ab')$_2$Fv, scFv, Fd, diabodies, single-chain antibodies, and other antibody fragments that retain at least a portion of the variable region of an intact antibody), a receptor, a ligand, aptamers, antibody substitute proteins or peptides (i.e., engineered binding proteins/peptides), molecular imprinted polymers (i.e., inorganic matrices), combinations or derivatives thereof, as well as any other molecules capable of specific binding to the analyte.

Turning now to particular embodiments of the presently claimed and disclosed inventive concept(s), assay compositions as well as kits containing same and methods of use thereof are disclosed. In some assay embodiments, signal producing system (sps) members comprise an electrode and a chemiluminescent composition, where excitation of the electrode results in a product that activates the chemiluminescent composition. One sps member usually generates a detectable signal that relates to the amount of bound and/or unbound sps member, i.e., the amount of sps member bound or not bound to the analyte being detected or to an agent that reflects the amount of the analyte to be detected. An exemplary embodiment of an assay platform on which the presently disclosed and claimed inventive concept(s) is based is the induced luminescence immunoassay (LOCI®). The induced luminescence immunoassay is described in U.S. Pat. No. 5,340,716 (Ullman), the entire contents of which are expressly incorporated herein by reference.

The presently disclosed and claimed inventive concept(s) provides a new method of generating singlet oxygen when compared to the currently available LOCI® assay, by eliminating the sensibead of the current technology and replacing it with an electrode. A sandwich complex (formed of target analyte directly or indirectly bound to a chemiluminescent compound) is captured on the electrode (via the direct or indirect binding of the target analyte thereto, as described in greater detail herein below). Once the complex is captured, the mixture may be washed, if desired, thus providing a heterogeneous assay format in which all nonspecifically bound particles can be washed away. A singlet oxygen generator molecule may then be washed over the captured complex, and a potential may be applied to the electrode. This causes the generation of singlet oxygen that reacts only with the captured chemiluminescent compound, thus generating a light signal. In this manner, the instrument system utilized is simplified, as no tight source is required to generate singlet oxygen. In addition, the replacement of the sensibead with the electrode eliminates any non-specific sensibead-chemibead (i.e., chemiluminescent compound) cross-talk, thereby providing an assay format with very low background signal as well as high sensitivity.

In a first embodiment, the presently disclosed and claimed inventive concept(s) is directed to a composition containing a chemiluminescent detection system. The composition includes an electrode capable of directly or indirectly binding to a target analyte and capable of generating singlet oxygen in its excited state. The composition may further include a composition comprising a singlet oxygen-activatable chemiluminescent compound capable of directly or indirectly binding to the target analyte and/or a composition comprising a singlet oxygen generator.

In a second embodiment, the presently disclosed and claimed inventive concept(s) is directed to a composition containing a competitive chemiluminescent detection system. Said composition is similar to the above-described composition, except that either the electrode or the composition comprising the singlet oxygen-activatable chemiluminescent compound is provided with target analyte or an analog thereof bound thereto that competes with target analyte present in a sample for binding to the other component.

Any of the compositions described above or otherwise contemplated herein may further include a wash solution. In addition, any of the compositions described herein above or otherwise contemplated herein may also include a microfluidics device in which one or more of the above-described components are disposed.

The term "electrode" as used herein refers to any type of conductor or medium that is capable of functioning in accordance with the presently disclosed and claimed inventive concept(s). Non-limiting examples of electrodes that fall within the scope of the presently disclosed and claimed inventive concept(s) include electrochemical cells comprising a plurality of electrodes. Exemplary electrochemical cell constructs include a two-electrode cell comprising one indicator electrode and one reference electrode, a two-electrode cell comprising one anode and one cathode, a three-electrode cell comprising one anode, one cathode and one reference electrode, and a four-electrode cell comprising two working electrodes, one counter electrode, and one reference electrode.

The term "singlet oxygen generator" as used herein refers to any compound that is capable of generating singlet oxygen in accordance with the presently disclosed and claimed inventive concept(s). Non-limiting examples of singlet oxygen generators that fall within the scope of the presently disclosed and claimed inventive concept(s) include Rose Bengal, Methylene Blue, Eosin, Porphyrin(s), and Phthalocyanines, and combinations thereof.

A chemiluminescent compound (chemiluminescer) is a compound that is chemically activatable and, as a result of such activation, emits light at a certain wavelength. Examples of chemiluminescers, by way of illustration and not limitation, include olefins capable of reacting with singlet oxygen or a peroxide to form hydroperoxides or dioxetanes, which can decompose to ketones or carboxylic acid derivatives; stable dioxetanes which can decompose by the action of light; acetylenes which can react with singlet oxygen to form diketones; hydrazones hydrazides that can form azo compounds or azo carbonyls such as luminol; and aromatic compounds that can form endoperoxides, for example. As a consequence of the activation reaction, the chemiluminescers directly or indirectly cause the emission of light.

In certain embodiments, the singlet oxygen-activatable chemiluminescent compound may be a substance that undergoes a chemical reaction with singlet oxygen to form a metastabile intermediate species that can decompose with the simultaneous or subsequent emission of light. The composition comprising the singlet oxygen-activatable chemiluminescent compound may associate with the target analyte by any method known in the art; for example but not by way of limitation, the composition may have a second analyte-specific binding partner associated therewith that allows for the indirect association of the chemiluminescent compound to the target analyte. The composition comprising the chemiluminescent compound may be directly excited by the activated chemiluminescent compound; alternatively, the composition may further comprise at least one fluorescent molecule that is excited by the activated chemiluminescent compound. Particular, non-limiting examples of chemiluminescent compounds that may be utilized in accordance with the presently disclosed and claimed inventive concept(s) are set forth in U.S. Pat. No. 5,340,716 (Ullman, et al.), the entire contents of which are hereby expressly incorporated herein by reference.

In certain embodiments of the presently disclosed and claimed inventive concept(s), the electrode may be capable of indirectly binding to the target analyte via an association with streptavidin (i.e., a streptavidin coating disposed on at least a portion of a surface of the electrode). In this manner, biotin is associated with a first analyte-specific binding partner, and the binding of streptavidin and biotin, in combination with the binding of the first analyte-specific binding partner to the target analyte, results in the indirect association of the electrode to the target analyte.

The reagents of the compositions/kits/methods may be provided in any form that allows them to function in accordance with the presently disclosed and claimed inventive concept(s). For example but not by way of limitation, the reagents may be disposed in the form of single aliquot lyophilized reagents. The use of dried reagents in microfluidics devices is described in detail in co-pending application U.S. Ser. No. 61/562,677, the entire contents of which are hereby expressly incorporated herein by reference.

The presently disclosed and claimed inventive concept(s) further includes kits useful for conveniently performing an assay for the determination of an analyte; the kit may contain any combination of the above-described components/reagents; in addition, the kit may further contain other reagent(s) for conducting any of the particular assays described or otherwise contemplated herein. The nature of these additional reagent(s) will depend upon the particular assay format, and identification thereof is well within the skill of one of ordinary skill in the art.

The components/reagents may each be in separate containers/compartments, or various components/reagents can be combined in one or more containers/compartments, depending on the cross-reactivity and stability of the components/reagents. The kit can further include other separately packaged reagents for conducting an assay, such as additional sbp members, sps members and ancillary reagents, for example. In addition, the kit may include a microfluidics device in which the components/reagents are disposed.

The relative amounts of the various components/reagents in the kits can vary widely to provide for concentrations of the components/reagents that substantially optimize the reactions that need to occur during the assay methods and further to optimize substantially the sensitivity of an assay. Under appropriate circumstances one or more of the components/reagents in the kit can be provided as a dry powder, such as a lyophilized powder, and the kit may further include excipient(s) for dissolution of the dried reagents; in this manner, a reagent solution having the appropriate concentrations for performing a method or assay in accordance with the presently disclosed and claimed inventive concept(s) can be obtained from these components. Positive and/or negative controls may be included with the kit. The kit can further include a set of written instructions explaining how to use the kit. A kit of this nature can be used in any of the methods described or otherwise contemplated herein.

The presently disclosed and claimed inventive concept(s) is further directed to a microfluidics device that includes a sample application chamber in which a sample may be applied and an inlet channel in fluidic communication therewith that is also in fluidic communication with one or more compartments containing one or more of the components described herein above (i.e., electrode (with or without target analyte (or an analog thereof) attached thereto), composition comprising singlet oxygen-activatable chemiluminescent compound, and composition comprising singlet oxygen generator). The device may be provided with any arrangement of the compartments and distribution of the component(s) there between that allows the device to function in accordance with the presently disclosed and claimed inventive concept(s); non-limiting examples of device structure are provided in the Figures for illustrative purposes only.

Any of the compartments of the microfluidics device may be sealed to maintain reagent(s) disposed therein in a substantially air tight environment until use thereof; for example, compartments containing lyophilized reagent(s) may be sealed to prevent any unintentional reconstitution of the reagent. The inlet channel and a compartment, as well as two compartments, may be described as being "capable of being in fluidic communication" with one another; this phrase indicates that the compartment(s) may still be sealed, but the two compartments are capable of having fluid flow there between upon puncture of a seal formed therein or there between.

The microfluidics devices of the presently disclosed and claimed inventive concept(s) may be provided with any other desired features known in the art or otherwise contemplated herein. For example but not by way of limitation, the microfluidics devices of the presently disclosed and claimed inventive concept(s) may further include a read chamber. The read chamber may be the compartment in which the electrode is disposed, or the read chamber may be capable of being in fluidic communication with the compartment in which the electrode is disposed. The microfluidics device may further include one or more compartments containing other solutions, such as but not limited to, wash solutions, dilution solutions, excipients, interference solutions, positive controls, negative controls, quality controls, and the like. For example, the microfluidics device may include one or more compartments containing a wash solution, and these compartment(s) may be capable of being in fluidic communication with any other compartment(s) of the device. In another example, the microfluidics device may further include one or more compartments containing at least one excipient for dissolution of one or more dried reagents, and the compartment(s) may be capable of being in fluidic communication with any other compartment(s) of the device. In a yet further example, the microfluidics device may further include one or more compartments containing a dilution solution, and the compartment(s) may be capable of being in fluidic communication with any other compartment(s) of the device.

In addition, any of the kits/microfluidics devices described or otherwise contemplated herein may include multiple assays multiplexed in a single kit/device. When multiple assays are present, both of the assays may be constructed and function as described herein. Alternatively, an assay as described herein may be multiplexed with any other assay known in the art that is capable of being contained within the kits/microfluidics devices of the presently disclosed and claimed inventive concept(s). Non-limiting examples of other assays that may be multiplexed with the assays disclosed and claimed herein include BNP, NT-proBNP, D-Dimer, CKMB, Myoglobin, Myeloperoxidase, ST2, PCT, hCG, LH, FSH, iPTH, TSH, $fT_4$, $T_4$, PSA, fPSA, and cPSA, and combinations thereof.

When multiple assays are present in a single microfluidics device, multiple inlet channels may be connected to the sample application chamber. In certain embodiments, a portion of the sample may be passed from the sample application chamber to the multiple inlet channels without regard for the content thereof. Alternatively, structure(s) may be present in the sample application chamber, the inlet channels, and/or the connection there between that allow for separation of certain components from the whole sample and delivery of said components to the different assays. A non-limiting example of a sample distribution device that may be utilized in accordance with the presently disclosed and claimed inventive concept(s) is described in detail in Provisional Application No. 61/790,580, filed Mar. 15, 2013, entitled "Microfluidic Distributing Device."

The presently disclosed and claimed inventive concept(s) is further directed to a method for detecting the presence and/or concentration of a target analyte in a sample (such as but not limited to, whole blood, lysed whole blood cells, or red blood cells). In one embodiment, the method includes the steps of combining, either simultaneously or wholly or partially sequentially: a sample suspected of containing the target analyte, the electrode, composition comprising the singlet oxygen-activatable chemiluminescent compound, and the composition comprising the singlet oxygen generator, each as described herein above. The composition comprising the chemiluminescent compound and the electrode are allowed to bind to the target analyte, whereby the sandwich complex is formed, and the electrode is brought into close proximity to the chemiluminescent compound. The sandwich complex is then washed with a composition comprising a singlet oxygen generator, and a potential is applied to the electrode to generate singlet oxygen, wherein generation of singlet oxygen in dose proximity to the chemiluminescent compound causes the activation of the chemiluminescent compound present in the sandwich complex. The amount of chemiluminescence generated by the activated chemiluminescent compound is then determined, and any of the above steps may optionally be repeated for a desired number of times. The presence and/or concentration of the target analyte are detected by analyzing the amount of chemiluminescence so produced, wherein the amount of chemiluminescence is directly proportional to the amount of analyte in the sample.

In another embodiment, a competitive method is provided and the electrode has target analyte or an analog thereof attached thereto. In this manner, the composition comprising the singlet oxygen-activatable chemiluminescent compound is allowed to bind to either the target analyte (or analog thereof) bound to the electrode or target analyte present in the sample. The binding of the composition comprising the singlet oxygen-activatable chemiluminescent compound to the target analyte (or analog thereof) bound to the electrode brings the electrode into close proximity to the chemiluminescent compound, whereas the binding of the composition comprising the singlet oxygen-activatable chemiluminescent compound to target analyte present in the sample prevents association thereof with the electrode. The remainder of the method is performed as described herein above, and the presence and/or concentration of the target analyte is detected by analyzing the amount of chemiluminescence so produced, wherein the amount of chemiluminescence is inversely proportional to the amount of target analyte in the sample.

In yet another embodiment of a competitive method, the composition comprising singlet-oxygen activatable chemiluminescent compound has target analyte or an analog thereof attached thereto. In this manner, the electrode is allowed to bind to either the target analyte (or analog thereof) bound to the composition comprising the singlet-oxygen activatable chemiluminescent compound or to target analyte present in the sample. The binding of the electrode to the target analyte (or analog thereof) bound to the composition comprising the singlet-oxygen activatable chemiluminescent compound brings the electrode into close proximity to the chemiluminescent compound, whereas the binding of the electrode to target analyte present in the sample prevents association of the electrode with the composition comprising the singlet-oxygen activatable chemiluminescent compound. The remainder of the method is performed as described herein above, and the presence and/or concentration of the target analyte is detected by analyzing the amount of chemiluminescence so produced, wherein the amount of chemiluminescence is inversely proportional to the amount of target analyte in the sample.

When the composition comprising the chemiluminescent compound includes a fluorescent molecule that is excited by the activated chemiluminescent compound, the method may further include the step of measuring the amount of light emitted by the fluorescent molecules to determine the amount of analyte in the sample.

As mentioned above, the various components of the method are provided in combination (either simultaneously or sequentially). When the various components of the method are added sequentially, the order of addition of the components may be varied; a person having ordinary skill in the art can determine the particular desired order of addition of the different components to the assay. The simplest order of addition, of course, is to add all the materials simultaneously and determine the signal produced therefrom. Alternatively, each of the components, or groups of components, can be combined sequentially. In certain embodiments, an incubation step may be involved subsequent to each addition as discussed above.

Certain embodiments of the presently disclosed and claimed inventive concept(s) include a heterogeneous assay; that is, certain embodiments of the method may further include one or more washing steps employed after an incubation step(s). When the reagents are added to the assay in a sequential format, the method may include multiple washing steps (i.e., after each reagent addition and incubation with the reaction). The washing step(s) functions to reduce background signal and potentially increase analytical sensitivity. For example but not by way of limitation, one embodiment of the method may further include the step of substantially washing away unbound or non-specifically bound sample and/or chemiluminescent compound from the electrode prior to applying a potential to the electrode.

Turning now to the Drawings, FIG. 1 depicts a first embodiment of a microfluidics device constructed in accordance with the presently disclosed and claimed inventive concept(s). The microfluidics device is indicated by the general reference numeral 10 and includes a housing 12 that includes a sample application chamber 14, an inlet channel 16, and a compartment/read chamber 18. A sample (such as, but not limited to, a blood sample) may be applied to the sample application chamber 14, which is in (or is capable of being in) fluidic communication with the inlet channel 16. The inlet channel 16 is in (or is capable of being in) fluidic communication with the compartment/read chamber 18. The compartment 18 contains an electrode 20, a predetermined amount of a composition 22 that includes a singlet oxygen-activatable chemiluminescent compound, and a predetermined amount of a composition 24 that includes a singlet oxygen generator. It will be understood that if the microfluidics device is utilized in a competitive assay format, the electrode 20 or the composition 24 may have target analyte or an analog thereof attached thereto.

The inlet channel 16 may simply transfer a portion of the sample to the compartment 18, or the inlet channel 16 may contain structure(s) that allow for separation of certain components from the whole sample (i.e., separation filter(s) that provide for separation of plasma or red blood cells from a whole blood sample applied to the sample application chamber 14) and/or detection of degradation (such as but not limited to, hemolysis) in the sample.

Figure 2:
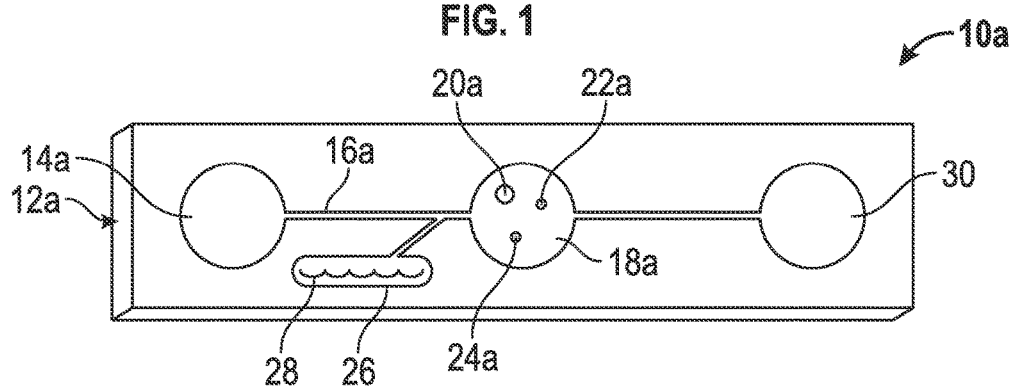
FIG. 2 illustrates a second embodiment of a microfluidic device constructed in accordance with the presently disclosed and claimed inventive concept(s).

Any of the microfluidics devices described or otherwise contemplated herein may be provided with additional compartments containing other reagents/solutions. For example, FIG. 2 depicts a microfluidics device 10a that is similar to the microfluidics device 10 of FIG. 1, with the exception that the microfluidics device 10a is provided with a heterogeneous assay format. That is, the microfluidics device 10a further includes a second compartment 26 that is in (or is capable of being in) fluidic communication with the inlet channel 16a and/or the first compartment 18a; the second compartment 26 contains a predetermined amount of wash solution 28. The microfluidics device 10a also further includes a waste compartment 30 that is in (or is capable of being in) fluidic communication with the first compartment 18a and receives the wash solution 28 once it has passed through the first compartment 18a. However, the use of a wash solution is not to be construed as limiting, and the presence within the device of any additional reagents described or contemplated herein or otherwise known in the art within one or more additional compartments also falls within the scope of the presently disclosed and claimed inventive concept(s).

Figure 3:
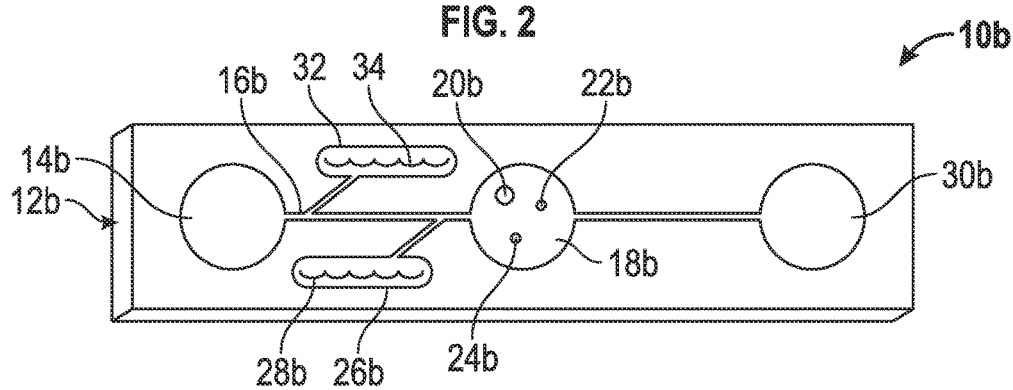
FIG. 3 illustrates a third embodiment of a microfluidic device constructed in accordance with the presently disclosed and claimed inventive concept(s).

FIG. 3 contains another example of a microfluidics device that is provided with additional compartments containing other reagents/solutions. When the reagents disposed in the compartment(s) (i.e., electrode (with or without target analyte (or an analog thereof) attached thereto), singlet oxygen-activatable chemiluminescent compound and/or singlet oxygen generator) are in the form of a dried reagent, the sample/plasma may be utilized for reconstitution thereof; alternatively, the microfluidics device may be provided with one or more compartments containing excipient that may be in (or may be capable of being in) fluidic communication with one or more of the compartment(s) containing said reagent(s). In FIG. 3, a microfluidics device 10b is shown that is similar to the microfluidics devices 10 and 10a of FIGS. 1-2, except that the microfluidics device 10b further includes a third compartment 32 that is in (or capable of being in) fluidic communication with the inlet channel 16b and/or the first compartment 18b and contains a predetermined amount of excipient 34 for reconstitution of at least one of the reagents 20b, 22b, and 24b. it is to be understood that the microfluidics device 10b is illustrated as having both the second and third compartments 26b and 32 for the purposes of example only. Any of the devices disclosed or otherwise contemplated herein may be provided with the wash solution-containing compartment alone or the excipient-containing compartment alone. Alternatively, any of the devices disclosed or otherwise contemplated herein may be provided with one or more wash solution-containing compartments and one or more excipient-containing compartments.

Any of the compartments of any of the microfluidics devices described or otherwise contemplated herein may be sealed to maintain reagent(s) disposed therein in a substantially air tight and/or substantially light tight environment until use thereof; for example, compartments containing lyophilized reagent(s) may be sealed to prevent any unintentional reconstitution of the reagent and/or exposure of any of the reagents to light. The inlet channel and a first compartment, as well as two compartments, may be described as being "capable of fluidic communication" with one another; this phrase indicates that the compartment(s) may still be sealed, but are capable of having fluid flow there between upon puncture of a seal formed therein.

In addition, it is to be understood that any of the microfluidics devices described or otherwise contemplated herein may further be provided with additional chambers and/or other fluidic circuits. For example but not by way of limitation, any of the microfluidics devices may additionally contain mixing chamber(s) and/or fluidic circuit(s) that are disposed between two reagent chambers.

Figure 4:
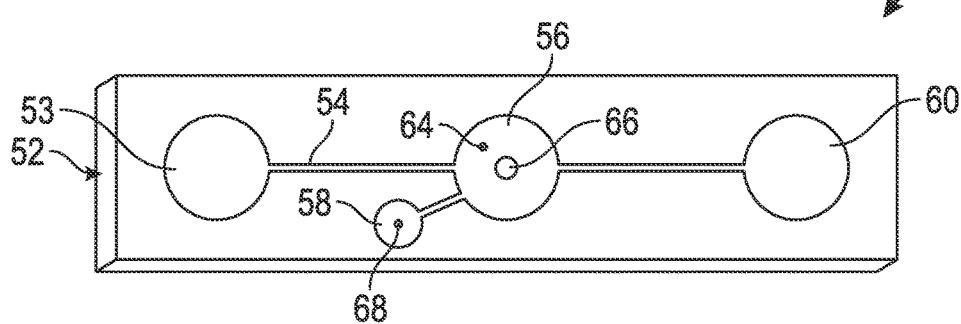
FIG. 4 illustrates another embodiment of a microfluidic device constructed in accordance with the presently disclosed and claimed inventive concept(s).

FIG. 4 depicts another embodiment of a microfluidics device constructed in accordance with the presently disclosed and claimed inventive concept(s). The microfluidics device is indicated by the general reference numeral 50 and is similar to the microfluidics devices 10, 10a and 10b of FIGS. 1-3, except that the microfluidics device 50 contains two compartments in which the three reagents (i.e., singlet oxygen-activatable chemiluminescent compound, singlet oxygen generator and/or electrode (with or without attached target analyte (or analog thereof)) are disposed.

The microfluidics device 50 includes a housing 52 that includes a sample application chamber 53, an inlet channel 54, a first compartment 56, a second compartment 58, and a waste compartment 60. A sample (such as, but not limited to, a blood sample) may be applied to the sample application chamber 53, which is in (or is capable of being in) fluidic communication with the inlet channel 54. The inlet channel 54 is in (or capable of being in) fluidic communication with the first compartment 56. The first compartment 56 contains a predetermined amount of a composition 64 that includes a singlet oxygen-activatable chemiluminescent compound and a predetermined amount of electrode 66 (with or without target analyte (or analog thereof) attached thereto). The second compartment 58 is in (or is capable of being in) fluidic communication with the inlet channel 54 and/or the first compartment 56; the second compartment 58 contains a predetermined amount of a composition 68 that includes a singlet oxygen generator. The first compartment 56 may further be defined as a read chamber and is in (or is capable of being in) fluidic communication with the waste compartment 60.

The order of distribution of the reagents 64, 66 and 68 in the compartments 56 and 58 is for the purposes of example only and should not be construed as limiting. The reagents 64, 66, and 68 may be distributed in the compartments 56 and 58 in any desired order. For example, the predetermined amount of the composition 64 may be disposed in the second compartment 58 along with the composition 68. The microfluidics device 50 may further be provided with one or more additional compartments containing wash solution(s) and/or excipient(s) (as described above with respect to FIGS. 2-3). When one or more additional compartments is provided, the compartments may be in (or may be capable of being in) fluidic communication with the inlet channel 54, the first compartment 56 and/or the second compartment 58. In addition, when the microfluidics device is used in a competitive assay format, the composition 64 or the electrode 66 may have target analyte (or an analog thereof) attached thereto.

Figure 5:
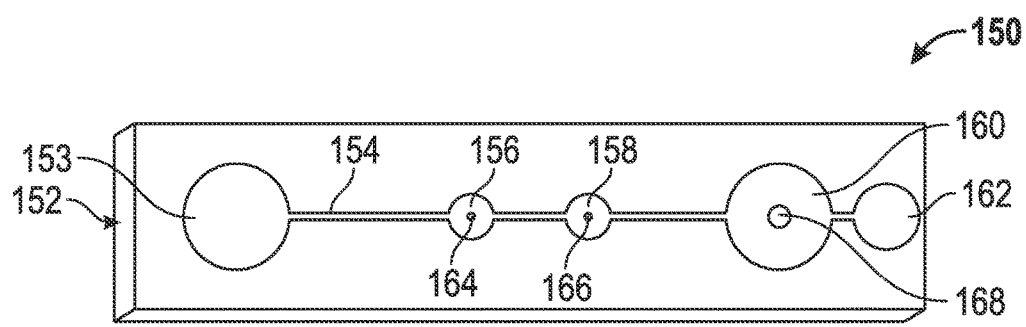
FIG. 5 illustrates another embodiment of a microfluidic device constructed in accordance with the presently disclosed and claimed inventive concept(s).

FIG. 5 depicts another embodiment of a microfluidics device constructed in accordance with the presently disclosed and claimed inventive concept(s). The microfluidics device is indicated by the general reference numeral 150 and is similar to the microfluidics devices 10, 10a, 10b, and 50 of FIGS. 1-4, except that the microfluidics device 150 contains three compartments in which the three reagents (i.e., singlet oxygen-activatable chemiluminescent compound, singlet oxygen and/or electrode (with or without attached target analyte (or an analog thereof))) are disposed.

The microfluidics device 150 includes a housing 152 that includes a sample application chamber 153, an inlet channel 154, a first compartment 156, a second compartment 158, a third compartment 160, and a waste compartment 162. A sample (such as, but not limited to, a blood sample) may be applied to the sample application chamber 153, which is in (or is capable of being in) fluidic communication with the inlet channel 154. The inlet channel 154 is in (or capable of being in) fluidic communication with the first compartment 156. The first compartment 156 contains a predetermined amount of a composition 164 that includes a singlet oxygen-activatable chemiluminescent compound. The second compartment 158 is in (or is capable of being in) fluidic communication with the first compartment 156; the second compartment 158 contains a predetermined amount of a composition 166 that includes a singlet oxygen generator. The third compartment 160 is in (or is capable of being in) fluidic communication with the second compartment 158; the third compartment 160 contains a predetermined amount of an electrode 168. The third compartment 160 may further be defined as a read chamber and is in (or is capable of being in) fluidic communication with the waste compartment 162. It will be understood that when the microfluidics device 150 is utilized in a competitive assay format, the composition 164 or the electrode 168 may have target analyte (or an analog thereof) attached thereto.

The order of distribution of the reagents 164, 166, and 168 in the compartments 156, 158, and 160 is for the purposes of example only and should not be construed as limiting. The reagents 164, 166, and 168 may be distributed in the compartments 156, 158, and 160 in any desired order.

Figure 6:
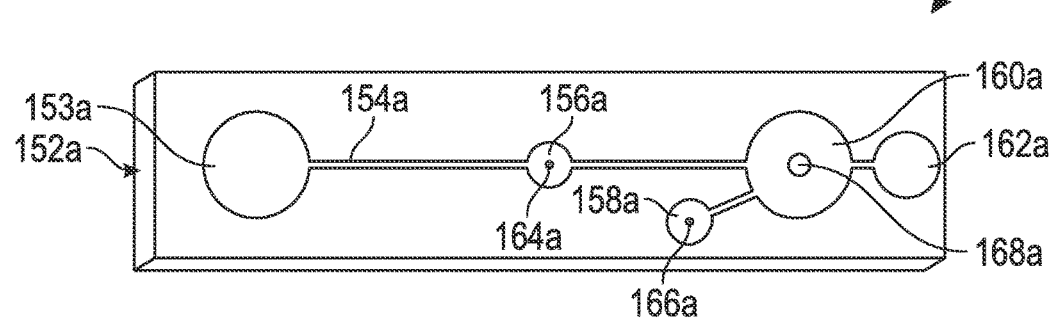
FIG. 6 illustrates yet another embodiment of a microfluidic device constructed in accordance with the presently disclosed and claimed inventive concept(s).

FIG. 6 depicts another embodiment of a microfluidics device constructed in accordance with the presently disclosed and darned inventive concept(s). The microfluidics device is indicated by the general reference numeral 150a and is similar to the microfluidics device 150 of FIG. 5, except that the microfluidics device 150a is provided with a different configuration for the three compartments thereof.

The microfluidics device 150a includes three compartments 156a, 158a and 160a that contain reagents 164a, 166a, and 168a, respectively. However, the first and second compartments 156a and 158a are not in fluidic communication with one another; instead, both the first and second compartments 156a and 158a are in (or are capable of being in) fluidic communication with the third compartment 160a.

Figure 7:
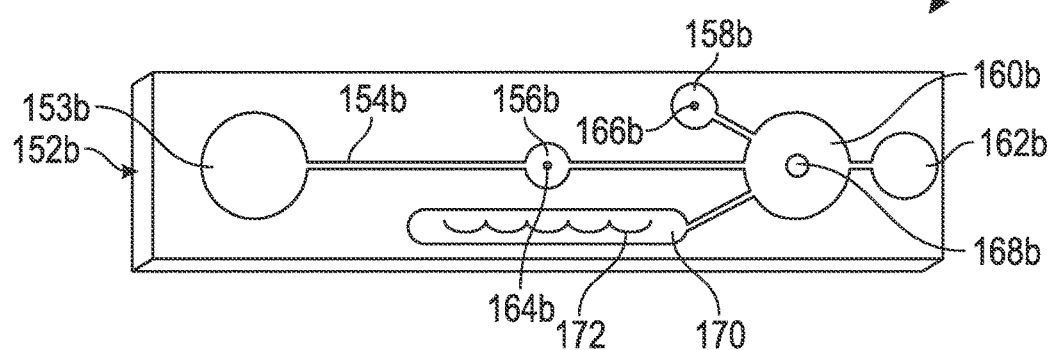
FIG. 7 illustrates yet another embodiment of a microfluidic device constructed in accordance with the presently disclosed and claimed inventive concept(s).

FIG. 7 depicts yet another embodiment of a microfluidics device constructed in accordance with the presently disclosed and claimed inventive concept(s). The microfluidics device is indicated by the general reference numeral 150b and is similar to the microfluidics device 150a of FIG. 6, except that the microfluidics device 150b is provided with a fourth compartment 170 that contains a predetermined amount of wash solution 172. The fourth compartment 170 is illustrated as being in (or capable of being in) fluidic communication with the third compartment 160b; however, it is to be understood that the fourth compartment 170 may be in (or may be capable of being in) fluidic communication with any of the compartments 156b, 158b, and/or 160b and/or the inlet channel 154b. The presence of wash solution 172 in the fourth compartment 170 is for the purposes of example only; it is to be understood that the solution present in the fourth compartment 170 may be excipient or other desired reagent.

Figure 8:
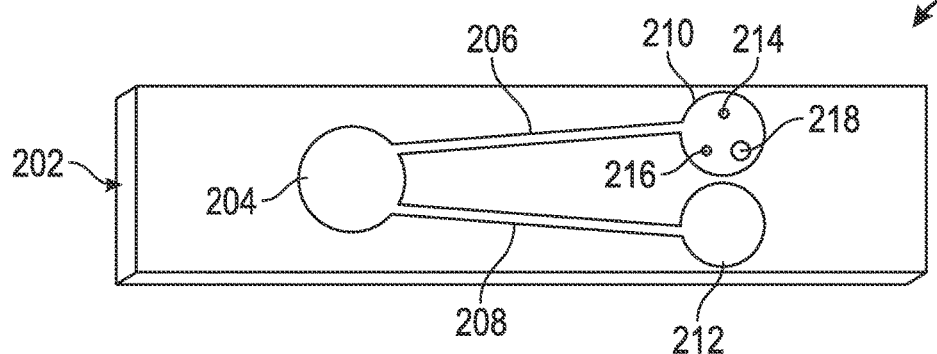
FIG. 8 illustrates yet another embodiment of a microfluidic device constructed in accordance with the presently disclosed and claimed inventive concept(s).

As stated herein above, any of the assay structures described herein above may be multiplexed with additional assay(s) in a single microfluidics device. FIG. 8 depicts yet another embodiment of a microfluidics device constructed in accordance with the presently disclosed and claimed inventive concept(s). The microfluidics device is indicated by the general reference numeral 200 and is similar to the microfluidics devices 10, 10a, 10b, 50, 150, 150a, and 150b of FIGS. 1-7, except that the microfluidics device 200 contains multiple compartments that provide a multiplexed assay format. The microfluidics device 200 includes a housing 202 that includes a sample application chamber 204, a first inlet channel 206, a second inlet channel 208, a first compartment 210, and a second compartment 212. A sample (such as, but not limited to, a blood sample) may be applied to the sample application chamber 204, which is in (or is capable of being in) fluidic communication with the inlet channels 206 and 208. The first inlet channel 206 is in (or capable of being in) fluidic communication with the first compartment 210. The first inlet channel 206 and the first compartment 210 represent the assay structure described in detail herein above (i.e., wherein the first compartment 210 contains a composition 214 that includes a singlet oxygen-activatable chemiluminescent compound, a composition 216 that includes a singlet oxygen generator, and an electrode 218). While this depicted assay structure is similar to that depicted in FIG. 1, it is to be understood that any of the other assay structures described herein above or otherwise contemplated herein may be utilized in the multiplexed assay microfluidics device. In addition, the microfluidics device 200 is provided with the second inlet channel 208 that is in (or capable of being in) fluidic communication with the second compartment 212. The second compartment 212 is simply provided to illustrate the presence of a second assay structure; it is to be understood that multiple compartments may be present as necessary to provide the required structure associated with the second assay. In addition, it should also be understood that the second compartment 212 may be provided with reagents similar to those present in the first compartment 210, so that multiple assays detecting different analytes by the same assay mechanism are present in the same microfluidics device. Alternatively, the second compartment 212 may represent a completely different assay format; the only requirement is that this second assay format be capable of being multiplexed with one of the assays described herein.

Thus, in accordance with the presently disclosed and claimed inventive concept(s), there has been provided compositions comprising a chemiluminescent system, as well as kits and microfluidics devices containing same and methods of use thereof, that fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A kit containing a chemiluminescent detection system for use with an instrument system, the chemiluminescent detection system comprising:
    (a) an electrode that specifically binds (directly or indirectly) to a target analyte, wherein the electrode has a potential applied thereto and generates singlet oxygen in its excited state;
    (b) a composition comprising a singlet oxygen-activatable chemiluminescent compound capable of directly or indirectly binding to the target analyte; and
    (c) a composition comprising a singlet oxygen generator;
    (d) a microfluidics device in which (a), (b), and (c) are disposed; and
    wherein application of the potential to (a) by the instrument system and in the presence of (c) causes generation of singlet oxygen in the absence of a light source, and wherein the singlet oxygen reacts with (b), thus generating a detectable amount of chemiluminescence; and
    wherein the electrode is disposed in a read chamber of the microfluidics device, and wherein the read chamber can be interrogated by the instrument system for detecting the amount of chemiluminescence produced.

2. The kit of claim 1, wherein at least a portion of a surface of the electrode is provided with a streptavidin coating disposed thereon, and wherein biotin is associated with a first analyte-specific binding partner, whereby the binding of streptavidin and biotin and the binding of the first analyte-specific binding partner to the target analyte results in the indirect association of the electrode to the target analyte.

3. The kit of claim 1, wherein the composition comprising the singlet oxygen-activatable chemiluminescent compound has a second analyte specific binding partner associated therewith that allows for the indirect association of the chemiluminescent compound to the target analyte.

4. The kit of claim 1, wherein the composition comprising the the singlet oxygen-activatable chemiluminescent compound further comprises at least one fluorescent molecule that is excited by the singlet oxygen-activatable chemiluminescent compound.

5. The kit of claim 1, wherein the electrode and the composition comprising the singlet oxygen-activatable chemiluminescent compound has target analyte or an analog thereof attached thereto.

6. A microfluidics device for disposal within an instrument system, the microfluidics device comprising:
    (a) an inlet channel through which a sample is applied;
    (b) at least one compartment capable of being in fluidic communication with the inlet channel, the at least one compartment containing:
        (i) an electrode that specifically binds (directly or indirectly) to a target analyte, wherein the electrode has a potential applied thereto and generates singlet oxygen in its excited state;
        (ii) a composition comprising a singlet oxygen-activatable chemiluminescent compound capable of directly or indirectly binding to the target analyte; and
        (iii) a composition comprising a singlet oxygen generator; and
    wherein application of a potential to (i) by the instrument system and in the presence of (iii) causes generation of singlet oxygen in the absence of a light source, and wherein the singlet oxygen reacts with (ii), thus generating a detectable amount of chemiluminescence; and
    wherein the electrode is disposed in a read chamber, and wherein the read chamber can be interrogated by the instrument system for detecting the amount of chemiluminescence produced.

7. The microfluidics device of claim 6, wherein one of:
    (a) the electrode has target analyte or an analog thereof attached thereto, whereby the composition comprising the singlet oxygen-activatable chemiluminescent compound is capable of directly or indirectly binding to target analyte present in a sample or to target analyte or analog thereof attached to the electrode; and
    (b) the composition comprising the singlet oxygen-activatable chemiluminescent compound has target analyte or an analog thereof attached thereto, whereby the electrode is capable of directly or indirectly binding to target analyte present in a sample or to target analyte or analog thereof attached to the composition comprising the singlet oxygen-activatable chemiluminescent compound.

8. The microfluidics device of claim 6, wherein (ii) and/or (iii) are disposed in at least one other compartment that is different from a compartment containing (i), and wherein the compartment containing (i) and the at least one other compartment containing (ii) and/or (iii) are capable of being in fluidic communication with one another.

9. The microfluidics device of claim 6, wherein at least one of the composition of (ii) or (iii) is lyophilized.

10. The microfluidics device of claim 9, further comprising at least one additional compartment capable of being in fluidic communication with at least one other compartment, wherein the at least one additional compartment contains an excipient for reconstitution of the at least one lyophilized reagent.

11. The microfluidics device of claim 6, wherein at least a portion of a surface of the electrode is provided with a streptavidin coating disposed thereon, and wherein biotin is associated with a first analyte-specific binding partner, whereby the binding of streptavidin and biotin and the binding of the first analyte-specific binding partner to the target analyte results in the indirect association of the electrode to the target analyte.

12. A method for detecting the presence and/or concentration of a target analyte in a sample, comprising the steps of:
    (a) combining, either simultaneously or wholly or partially sequentially:
        (1) a sample suspected of containing the target analyte;
        (2) an electrode capable of directly or indirectly binding to the target analyte and capable of generating singlet oxygen in its excited state; and
        (3) a composition comprising a singlet oxygen-activatable chemiluminescent compound capable of directly or indirectly binding to the target analyte;
    (b) allowing the binding of the composition comprising the chemiluminescent compound and the electrode to the target analyte, whereby a sandwich complex is formed by the binding of (2) and (3) to the target analyte such that the electrode is brought into close proximity to the chemiluminescent compound;

(c) washing the electrode with a composition comprising a singlet oxygen generator;

(d) applying a potential to the electrode to generate singlet oxygen, wherein generation of singlet oxygen in close proximity to the chemiluminescent compound causes the activation of the chemiluminescent compound present in the sandwich complex, thus generating a detectable signal in the absence of a light source;

(e) determining the amount of chemiluminescence generated by the activated chemiluminescent compound;

(f) optionally repeating steps (b)-(e); and (g) detecting the presence and/or concentration of the target analyte by analyzing the amount of chemiluminescence so produced, wherein the amount of chemiluminescence is directly proportional to the amount of target analyte in the sample.

13. The method of claim 12, wherein at least a portion of a surface of the electrode is provided with a streptavidin coating disposed thereon, and wherein biotin is associated with a first analyte-specific binding partner, whereby the binding of streptavidin and biotin and the binding of the first analyte-specific binding partner to the target analyte results in the indirect association of the electrode to the target analyte.

14. The method of claim 12, wherein the composition comprising the singlet oxygen-activatable chemiluminescent compound has a second analyte-specific binding partner associated therewith that allows for the indirect association of the chemiluminescent compound to the target analyte.

15. The method of claim 12, wherein the singlet oxygen-activatable chemiluminescent compound is a substance that undergoes a chemical reaction with singlet oxygen to form a metastabile intermediate species that can decompose with the simultaneous or subsequent emission of light.

16. The method of claim 12, further comprising the step of substantially washing away unbound or non-specifically bound (1) and (3) compositions from the electrode after step (b).

17. The method of claim 12, wherein the composition comprising the chemiluminescent compound further comprises at least one fluorescent molecule that is excited by the activated chemiluminescent compound.

* * * * *